United States Patent
Ritzeler et al.

(10) Patent No.: US 7,342,029 B2
(45) Date of Patent: *Mar. 11, 2008

(54) SUBSTITUTED INDOLES

(75) Inventors: Olaf Ritzeler, Frankfurt am Main (DE);
Hans Ulrich Stilz, Frankfurt (DE);
Bernhard Neises, Offenburg (DE);
Gerhard Jaehne, Frankfurt (DE);
Joerg Habermann, Bad Soden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/187,396

(22) Filed: Jul. 22, 2005

(65) Prior Publication Data
US 2005/0282866 A1    Dec. 22, 2005

Related U.S. Application Data

(63) Continuation of application No. 10/842,427, filed on May 11, 2004, now abandoned, which is a continuation of application No. 10/263,691, filed on Oct. 4, 2002, now abandoned, which is a continuation of application No. 09/695,412, filed on Oct. 25, 2000, now abandoned.

(30) Foreign Application Priority Data
Oct. 26, 1999    (DE) ................ 199 51 360

(51) Int. Cl.
A61K 31/44     (2006.01)
A61K 31/405    (2006.01)
C07D 209/04    (2006.01)

(52) U.S. Cl. ............... 514/339; 514/415; 548/481
(58) Field of Classification Search ........ 514/339, 514/415; 548/491, 277.4; 546/277.4
See application file for complete search history.

(56) References Cited

U.S. PATENT DOCUMENTS

| 5,723,485 | A | 3/1998 | Gungor et al. |
| 5,834,493 | A | 11/1998 | Gil Quintero et al. |
| 5,849,765 | A | 12/1998 | Curtis et al. |
| 6,310,217 | B1 | 10/2001 | Lehr |
| 6,358,978 | B1 | 3/2002 | Ritzeler et al. |
| 2004/0116494 | A1 | 6/2004 | Michaelis et al. |
| 2005/0197353 | A1 | 9/2005 | Ritzeler et al. |

FOREIGN PATENT DOCUMENTS

| JP | 06239841 | * | 8/1994 |
| WO | WO 94/08962 | | 4/1994 |
| WO | WO 94/12478 | | 6/1994 |
| WO | WO 98/05637 | | 2/1998 |
| WO | WO 98/22457 | | 5/1998 |
| WO | WO 99/24035 | | 5/1999 |
| WO | WO 99/43654 | | 9/1999 |
| WO | WO 2005/113544 | | 12/2005 |

OTHER PUBLICATIONS

U.S. Appl. No. 10/642,970.*
Co-pending U.S. Appl. No. 10/642,970.*
copending U.S. Appl. No. 10/642,970.*
Kocienski, Philip, Protecting Groups, Thieme Verlag, 1994, pp. 7, 205, 206, 207, 222 and 259.

* cited by examiner

Primary Examiner—Rebecca Anderson
Assistant Examiner—Susannah Chung
(74) Attorney, Agent, or Firm—Julie Anne Knight; Robert J. Kajubi; James W. Bolcsak

(57) ABSTRACT

Compounds of the formula I

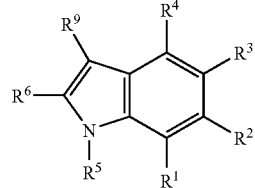

(I)

are suitable for preparing pharmaceuticals for the prophylaxis and therapy of disorders in whose course an increased activity of NFκB is involved.

8 Claims, No Drawings

SUBSTITUTED INDOLES

This is a continuation of application Ser. No. 10/842,427, filed May 11, 2004, now abandoned, which is a continuation of application Ser. No. 10/263,691, filed Oct. 4, 2002, now abandoned, which is a continuation of application Ser. No. 09/695,412, filed Oct. 25, 2000, now abandoned, all of which are incorporated by reference.

The invention relates to novel substituted indoles, to processes for their preparation and to their use as pharmaceuticals.

The application WO 94/12478 describes, inter alia, indole derivatives which inhibit blood platelet aggregation.

NFκB is a heterodimeric transcription factor which can activate a large number of genes which code, inter alia, for proinflammatory cytokines such as IL-1, IL-2, TNFα or IL-6. NFκB is present in the cytosole of cells, complexed with its naturally occurring inhibitor IκB. The stimulation of cells, for example by cytokines, leads to the phosphorylation and subsequent proteolytic degradation of IκB. This proteolytic degradation leads to the activation of NFκB, which subsequently, migrates into the nucleus of the cell and there activates a large number of proinflammatory genes.

In disorders such as rheumatoid arthritis (in the case of inflammation), osteoarthritis, asthma, cardiac infarct, Alzheimer's disease or athero-sclerosis, NFκB is activated beyond the normal extent. The inhibition of NFκB is also of benefit in cancer therapy, since it is employed there for the reinforcement of the cytostatic therapy. It was possible to show that pharmaceuticals such as glucocorticoids, salicylates or gold salts, which are employed in rheumatic therapy, intervene in an inhibitory manner at various points in the NFκB-activating signal chain or interfere directly with the transcription of the genes.

The first step in the signal cascade mentioned is the degradation of IκB. This phosphorylation is regulated by the specific IκB kinase. To date, no inhibitors are known which specifically inhibit IκB kinase.

In an attempt to obtain active compounds for the treatment of rheumatoid arthritis (in the case of inflammation), osteoarthritis, asthma, cardiac infarct, Alzheimer's disease, carcinomateous disorders (potentiation of cytotoxic therapies) or atherosclerosis, it has now been found that the indole derivatives according to the invention are potent and very specific inhibitors of IκB kinase.

The invention therefore relates to the compounds of the formula I

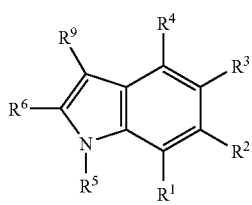

(I)

and/or a stereoisomeric form of the compound of the formula I and/or a physiologically acceptable salt of the compound of the formula I, where one of the substituents $R^1$, $R^2$, $R^3$ and $R^4$ is a radical of the formula II

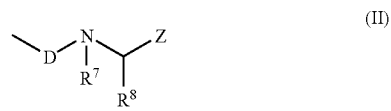

(II)

in which D is —C(O)—, —S(O)— or —S(O)$_2$—,
$R^7$ is hydrogen or —(C$_1$-C$_4$)-alkyl,
$R^8$ is $R^9$ or the characteristic radical of an amino acid,
$R^9$ is
1. aryl, where aryl is unsubstituted or substituted,
2. heteroaryl having 5 to 14 ring members, where heteroaryl is unsubstituted or substituted,
3. heterocycle having 5 to 12 ring members, where heterocycle is unsubstituted or substituted, or
4. —(C$_1$-C$_6$)-alkyl, where alkyl is straight-chain or branched and is unsubstituted or mono-, di- or trisubstituted, independently of one another, by
  4.1 aryl, where aryl is unsubstituted or substituted,
  4.2 heteroaryl having 5 to 14 ring members, where heteroaryl is unsubstituted or substituted,
  4.3 heterocycle having 5 to 12 ring members, where heterocycle is unsubstituted or substituted,
  4.4 —O—$R^{10}$,
  4.5 =O,
  4.6 halogen,
  4.7 —CN,
  4.8 —CF$_3$,
  4.9 —S(O)$_x$—$R^{10}$, where x is the integer zero, 1 or 2,
  4.10 —C(O)—O—$R^{10}$,
  4.11 —C(O)—N($R^{10}$)$_2$,
  4.12 —N($R^{10}$)$_2$,
  4.13 —(C$_3$-C$_6$)-cycloalkyl,
  4.14 radical of the formula

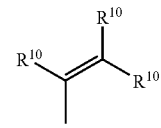

or
  4.15 radical of the formula

$R^{10}$ is a) hydrogen,
b) —(C$_1$-C$_6$)-alkyl, where alkyl is unsubstituted or mono- to trisubstituted, independently of one another, by
  1. aryl,
  2. heteroaryl having 5 to 14 ring members,
  3. heterocycle having 5 to 12 ring members,
  4. halogen,
  5. —N—(C$_1$-C$_6$)$_n$-alkyl, where n is the integer zero, 1 or 2 and alkyl is unsubstituted or mono-, di- or trisubstituted, independently of one another, by halogen or by —C(O)—OH, or
  6. —C(O)—OH,
c) aryl,
d) heteroaryl having 5 to 14 ring members or e) heterocycle having 5 to 12 ring members and, in the case of $(R^{10})_2$, $R^{10}$, independently of one another, has the meaning of a) to e), Z is 1. aryl, where aryl is unsubstituted or substituted,
2. heteroaryl having 5 to 14 ring members, where heteroaryl is unsubstituted or substituted,
3. heterocycle having 5 to 12 ring members, where heterocycle is unsubstituted or substituted, or
4. —C(O)—$R^{11}$, where $R^{11}$ is
   1. —O—$R^{10}$ or
   2. —N$(R^{10})_2$, or $R^7$ and $R^8$ form, together with the nitrogen atom and carbon atom to which they are each bonded, a heterocyclic ring of the formula IIa,

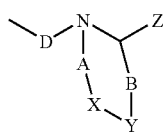

(IIa)

in which D, Z and $R^{11}$ are as defined in formula II,
A is a nitrogen atom or the radical —CH$_2$—,
B is an oxygen atom, sulfur atom, nitrogen atom or the radical —CH$_2$—,
X is an oxygen atom, sulfur atom, nitrogen atom or the radical —CH$_2$—,
Y is absent or is an oxygen atom, sulfur atom, sulfoatom or the radical —CH$_2$—, or
X and Y together form a phenyl, 1,2-diazine, 1,3-diazine or a 1,4-diazine radical, where the ring system formed by N, A, X, Y, B and the carbon atom contains not more than one oxygen atom, X is not an oxygen atom, sulfur or nitrogen atom if A is a nitrogen atom, contains not more than one sulfur atom, contains 1, 2, 3 or 4 nitrogen atoms and where an oxygen and sulfur atom do not occur at the same time, where the ring system formed by N, A, X, Y, B and the carbon atom is unsubstituted or mono- to trisubstituted, independently of one another, by —(C$_1$-C$_8$)-alkyl, unsubstituted or mono- to disubstituted by
1.1. —OH,
1.2. (C$_1$-C$_8$)-alkoxy,
1.3. halogen,
1.4. —NO$_2$,
1.5. —NH$_2$,
1.6. —CF$_3$,
1.7. —OH,
1.8 methylenedioxy,
1.9 —C(O)—CH$_3$,
1.10. —CH(O),
1.11. —CN,
1.12. —C(O)—OH,
1.13. —C(O)—NH$_2$,
1.14. (C$_1$-C$_4$)-alkoxycarbonyl,
1.15. phenyl,
1.16. phenoxy,
1.17. benzyl,
1.18. benzyloxy or
1.19. tetrazolyl, or $R^8$ and Z form, together with the carbon atoms to which they each are bonded, a heterocyclic ring of the formula IIc,

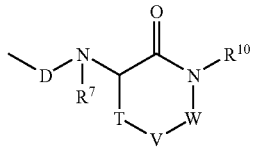

(IIc)

in which D, $R^7$ and $R^{10}$ are as defined in formula II,
T is an oxygen atom, sulfur atom, nitrogen atom or the radical —CH$_2$—,
W is an oxygen atom, sulfur atom, nitrogen atom or the radical —CH$_2$—,
V is absent or is an oxygen atom, sulfur atom, nitrogen atom or the radical —CH$_2$—, or
T and V or V and W together form a phenyl, 1,2-diazine, 1,3-diazine or a 1,4-diazine radical, where the ring system formed by N, T, V, W and two carbon atoms contains not more than one oxygen atom, not more than one sulfur atom and 1, 2, 3 or 4 nitrogen atoms, where an oxygen atom and sulfur atom do not occur at the same time, and where the ring system formed by N, T, V, W and two carbon atoms is unsubstituted or mono- to trisubstituted, independently of one another, by the substituents defined above under 1.1. to 1.19., and the respective other substituents $R^1$, $R^2$, $R^3$ and $R^4$ independently of one another are
1. hydrogen,
2. halogen,
3. aryl, where aryl is unsubstituted or substituted,
4. heteroaryl having 5 to 14 ring members, where heteroaryl is unsubstituted or substituted,
5. heterocycle having 5 to 12 ring members, where heterocycle is unsubstituted or substituted,
6. —(C$_1$-C$_6$)-alkyl,
7. —CN,
8. —O—$R^{10}$,
9. —N$(R^{10})_2$,
10. —S(O)$_x$—$R^{10}$, where x is the integer zero, 1 or 2, or
11. —CF$_3$, $R^5$ is 1. hydrogen,
2. —OH or
3. =O, and $R^6$ is 1. aryl, where aryl is unsubstituted or substituted,
2. heteroaryl having 5 to 14 ring members, where heteroaryl is unsubstituted or mono- to trisubstituted, or
3. heterocycle having 5 to 12 ring members, where heterocycle is unsubstituted or mono- to trisubstituted.

A preferred compound of the formula I is one where one of the substituents $R^1$, $R^2$, $R^3$ and $R^4$ is a radical of the formula II, in which
D is —C(O)—,
$R^7$ is hydrogen or —(C$_1$-C$_4$)-alkyl,
$R^8$ is 1. —(C$_1$-C$_4$)-alkyl, where alkyl is straight-chain or branched and is mono- or disubstituted, independently of one another, by
1.1 heteroaryl having 5 to 14 ring members, where heteroaryl is unsubstituted or substituted,
1.2 heterocycle having 5 to 12 ring members, where heterocycle is unsubstituted or substituted,
1.3 —O—$R^{10}$,
1.4 —S(O)$_x$—$R^{10}$, where x is the integer zero, 1 or 2,
1.5 —N$(R^{10})_2$, 1.6 radical of the formula

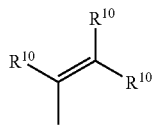

or
1.7 radical of the formula

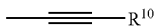

or
2. is the characteristic radical of an amino acid,
$R^9$ is 1. $R^8$,
  2. —($C_1$-$C_4$)-alkyl, where alkyl is straight-chain or branched and is, independently of one another, mono-, di- or trisubstituted by
    2.1 aryl, where aryl is unsubstituted or substituted,
    2.2 halogen,
    2.3 —CN or
    2.4 —$CF_3$ or
  3. aryl, where aryl is unsubstituted or substituted,
$R^{10}$ is a) hydrogen,
  b) —($C_1$-$C_6$)-alkyl, where alkyl is unsubstituted or mono- to trisubstituted, independently of one another, by
    1. aryl,
    2. heteroaryl having 5 to 14 ring members,
    3. heterocycle having 5 to 12 ring members,
    4. halogen,
    5. —N—($C_1$-$C_6$)$_n$-alkyl, where n is the integer zero, 1 or 2 and alkyl is unsubstituted or mono-, di- or trisubstituted, independently of one another, by halogen or by —C(O)—OH, or
    6. —C(O)—OH,
  c) aryl,
  d) heteroaryl having 5 to 14 ring members or
  e) heterocycle having 5 to 12 ring members and, in the case of ($R^{10}$)$_2$, $R^{10}$, independently of one another, has the meaning of a) to e),
Z is 1. 1,3,4-oxadiazole, where 1,3,4-oxadiazole is unsubstituted or mono- to trisubstituted by —$NH_2$, OH or —($C_1$-$C_4$)-alkyl or
  2. —C(O)—$R^{11}$, in which
$R^{11}$ is 1. —O—$R^{10}$ or
  2. —N($R^{10}$)$_2$, or
$R^7$ and $R^8$ form, together with the nitrogen atom and carbon atom to which they are each bonded, a ring of the formula IIa selected from the group consisting of pyrrole, pyrroline, indole, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, purine, isoxazole, 2-isoxazolidine, isoxazolidine, morpholine, isothiazole, thiazole, thiadiazole, benzimidazole, thiomorpholine, isothiazolidine, indazole, quinoline, triazole, phthalazine, quinazoline, quinoxaline, pteridine, tetrahydroquinoline, isoquinoline, 1,2,3,5-oxathiadiazole 2-oxides, tetrazole, oxadiazolones, isoxazolones, triazolones, oxadiazolidinediones, triazoles, which are substituted by F, —CN, —$CF_3$ or —C(O)—O—($C_1$-$C_4$)-alkyl, 3-hydroxypyrrole-2,4-diones, 5-oxo-1,2,4-thiadiazoles and tetrahydroisoquinoline, or $R^8$ and Z form, together with the carbon atoms to which they are each bonded, a ring of the formula IIc selected from the group consisting of pyrrole, pyrroline, pyrrolidine, pyridine, piperidine, piperylene, pyridazine, pyrimidine, pyrazine, piperazine, pyrazole, imidazole, pyrazoline, 1,3,4-oxadiazole, imidazoline, pyrazolidine, imidazolidine, oxazole, isoxazole, 2-isoxazolidine, isoxazolidine, morpholine, isothiazole, thiazole, isothiazolidine, tetrazole, thiomorpholine, indazole, thiadiazole, benzimidazole, quinoline, triazole, phthalazine, quinazoline, quinoxaline, purine, pteridine, indole, tetrahydroquinoline, triazolones, tetrahydroisoquinoline, 1,2,3,5-oxathiadiazole 2-oxides, oxadiazolones, isoxazolones, oxadiazolidindiones, triazoles, Which are substituted by F, —CN, —$CF_3$ or —C(O)—O—($C_1$-$C_4$)-alkyl, 3-hydroxypyrrole-2,4-diones, 5-oxo-1,2,4-thiadiazoles and isoquinoline, and the other substituents $R^1$, $R^2$, $R^3$ and $R^4$ in each case independently of one another are
  1. hydrogen,
  2. halogen,
  3. aryl, where aryl is unsubstituted or substituted,
  4. heteroaryl having 5 to 14 ring members, where heteroaryl is unsubstituted or substituted,
  5. heterocycle having 5 to 12 ring members, where heterocycle is unsubstituted or substituted, or
  6. —($C_1$-$C_6$)-alkyl,
  7. —CN,
  8. —$CF_3$,
  9. —O—$R^{10}$,
  10. —N($R^{10}$)$_2$, or
  11. —S(O)$_x$—$R^{10}$, where x is the integer zero, 1 or 2,
$R^5$ is hydrogen and
$R^6$ is 1. phenyl, mono- or disubstituted, independently of one another, by
    1.1 —CN,
    1.2 —$CF_3$ or
    1.3 halogen,
    1.4 —O—$R^{10}$,
    1.5 —N($R^{10}$)$_2$,
    1.6 —NH—C(O)—$R^{11}$,
    1.7 —S(O)$_x$—$R^{10}$, where x is the integer zero, 1 or 2,
    1.8 —C(O)—$R^{11}$ or
    1.9 —($C_1$-$C_4$)-alkyl-$NH_2$,
  2. heteroaryl having 5 to 14 ring members, where heteroaryl is unsubstituted or mono-, di- or trisubstituted, independently of one another, by the substituents defined above under 1.1 to 1.9 or
  3. heterocycle having 5 to 12 ring members, where heterocycle is unsubstituted or mono-, di- or trisubstituted, independently of one another, by the substituents defined above under 1.1 to 1.9.

A particularly preferred compound of the formula I is one where one of the substituents $R^1$, $R^2$, $R^3$ and $R^4$ is a radical of the formula II, in which
D is —C(O)—,
$R^7$ is hydrogen,
Z is —C(O)—OH or —C(O)—$NH_2$,
$R^8$ is 1. —($C_1$-$C_4$)-alkyl, where alkyl is straight-chain or branched and is mono- or disubstituted, independently of one another, by
    1.1 —S(O)—$R^{10}$, where $R^{10}$ is as defined below,
    1.2 —N($R^{10}$)$_2$, where $R^{10}$ is as defined below, or
    1.3 pyrrole or
  2. is the characteristic radical of an amino acid,
$R^{10}$ is a) hydrogen, b) —$(C_1-C_6)$-alkyl, where alkyl is unsubstituted or mono- to trisubstituted, independently of one another, by halogen,
c) phenyl, where phenyl is unsubstituted or mono- to trisubstituted, independently of one another, by halogen or —$(C_1-C_4)$-alkyl, in the case of $(R^{10})_2$, $R^{10}$, independently of one another, has the meaning of a) to c), the other substituents $R^1$, $R^2$, $R^3$ and $R^4$ in each case are hydrogen, $R^5$ is hydrogen,
$R^6$ is phenyl or pyridine, and
$R^9$ is 1. hydrogen,
   2. —$(C_1-C_4)$-alkyl, where alkyl is straight-chain or branched and, independently of one another, mono-, di- or trisubstituted by —C(O)OH, —OH or —C(O)—NH$_2$, or
   3. phenyl, where phenyl is unsubstituted or mono- to trisubstituted, independently of one another, by halogen or —$(C_1-C_4)$-alkyl.

The term "halogen" is understood as meaning fluorine, chlorine, bromine or iodine. The terms "$(C_1-C_8)$-alkyl", "$(C_1-C_6)$-alkyl" or "$(C_1-C_4)$-alkyl" are understood as meaning hydrocarbon radicals whose carbon chain is straight-chain or branched and contains 1 to 8, 1 to 6 and 1 to 4 carbon atoms, respectively. Cyclic alkyl radicals are, for example, 3- to 6-membered monocycles such as cyclopropyl, cyclobutyl, cyclopentyl or cyclohexyl.

The term "$R^7$ and $R^8$ form, together with the nitrogen atom and carbon atom to which they are each bonded, a heterocyclic ring of the formula IIa", is understood as meaning radicals which are derived from pyrrole, pyrroline, pyrrolidine, imidazole, pyrazole, oxazole, isoxazole, tetrazole, isoxazoline, isoxazolidine, morpholine, thiazole, isothiazole, isothiazoline, purine, isothiazolidine, thiomorpholine, pyridine, piperidine, pyrazine, piperazine, pyrimidine, pyridazine, indole, isoindole, indazole, benzimidazole, phthalazine, quinoline, isoquinoline, quinoxaline, quinazoline, cinnoline, pteridine, triazolones, tetrazole, 1,2,3,5-oxathiadiazole 2-oxides, oxadiazolones, isoxazolones, oxadiazolidine-diones, triazoles, which are substituted by F, —CN, —CF$_3$ or —C(O)—O—$(C_1-C_4)$-alkyl, 3-hydroxypyrrole-2,4-diones, 5-oxo-1,2,4-thiadiazoles, imidazolidine, carboline and benzo-fused derivatives of these heterocycles.

The term aryl is understood as meaning aromatic hydrocarbon radicals having 6 to 14 carbon atoms in the ring. $(C_6-C_{14})$-Aryl radicals are, for example, phenyl, naphthyl, for example 1-naphthyl, 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals. Aryl radicals, in particular phenyl radicals, can be monosubstituted or polysubstituted, preferably monosubstituted, disubstituted or trisubstituted, by identical or different radicals, preferably by radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, hydroxy-$(C_1-C_4)$-alkyl such as hydroxymethyl or 1-hydroxyethyl or 2-hydroxyethyl, methylenedioxy, ethylenedioxy, formyl, acetyl, cyano, hydroxycarbonyl, aminocarbonyl, $(C_1-C_4)$-alkoxycarbonyl, phenyl, phenoxy, benzyl, benzyloxy, tetrazolyl. The same applies, for example, to radicals such as arylalkyl or arylcarbonyl. Arylalkyl radicals are, in particular, benzyl and also 1- and 2-naphthylmethyl, 2-, 3- and 4-biphenylylmethyl and 9-fluorenylmethyl. Substituted arylalkyl radicals are, for example, benzyl radicals and naphthylmethyl radicals substituted in the aryl moiety by one or more $(C_1-C_8)$-alkyl radicals, in particular $(C_1-C_4)$-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-,4-, 5-, 6-, 7- and 8-methyl-1-naphthylmethyl, 1-, 3-, 4-, 5-, 6-, 7- and 8-methyl-2-naphthylmethyl, by one or more $(C_1-C_8)$-alkoxy radicals, in particular $(C_1-C_4)$-alkoxy radicals, benzyl radicals and naphthylmethyl radicals substituted in the aryl moiety, for example 4-methoxybenzyl, 4-neopentyloxybenzyl, 3,5-dimethoxybenzyl, 3,4-methylenedioxybenzyl, 2,3,4-trimethoxybenzyl, nitrobenzyl radicals, for example 2-, 3- and 4-nitrobenzyl, halobenzyl radicals, for example 2-, 3- and 4-chloro- and 2-, 3- and 4-fluorobenzyl, 3,4-dichlorobenzyl, pentafluorobenzyl, trifluoro-methylbenzyl radicals, for example 3- and 4-trifluoromethylbenzyl or 3,5-bis(trifluoromethyl)benzyl.

In monosubstituted phenyl radicals, the substituent can be located in the 2-position, the 3-position or the 4-position. Disubstituted phenyl can be substituted in the 2,3-position, the 2,4-position, the 2,5-position, the 2,6-position, the 3,4-position or the 3,5-position. In trisubstituted phenyl radicals, the substituents can be located in the 2,3,4-position, the 2,3,5-position, the 2,4,5-position, the 2,4,6-position, the 2,3,6-position or the 3,4,5-position.

The explanations for the aryl radicals apply accordingly to divalent arylene radicals, for example to phenylene radicals which can be present, for example, as 1,4-phenylene or as 1,3-phenylene.

Phenylene-$(C_1-C_6)$-alkyl is in particular phenylenemethyl (—C$_6$H$_4$—CH$_2$—) and phenyleneethyl, $(C_1-C_6)$-alkylenephenyl is in particular methylenephenyl (—CH$_2$—C$_6$H$_4$—). Phenylene-$(C_2-C_6)$-alkenyl is in particular phenyleneethenyl and phenylenepropenyl.

The expression "heteroaryl having 5 to 14 ring members" represents a radical of a monocyclic or polycyclic aromatic system having 5 to 14 ring members, which contains 1, 2, 3, 4 or 5 heteroatoms as ring members. Examples of heteroatoms are N, O and S. If a number of heteroatoms are contained, these can be identical or different. Heteroaryl radicals can likewise be monosubstituted or polysubstituted, preferably mono-substituted, disubstituted or trisubstituted, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, nitro, —N$(R^{10})_2$, trifluoromethyl, hydroxyl, hydroxy-$(C_1-C_4)$-alkyl such as hydroxymethyl or 1-hydroxyethyl or 2-hydroxyethyl, methylenedioxy, formyl, acetyl, cyano, hydroxycarbonyl, aminocarbonyl, $(C_1-C_4)$-alkoxycarbonyl, phenyl, phenoxy, benzyl, benzyloxy, tetrazolyl. Heteroaryl having 5 to 14 ring members preferably represents a monocyclic or bicyclic aromatic radical which contains 1, 2, 3 or 4, in particular 1, 2 or 3, identical or different heteroatoms from the group consisting of N, O and S and which can be substituted by 1, 2, 3 or 4, in particular 1 to 3, identical or different substituents from the group consisting of $(C_1-C_6)$-alkyl, $(C_1-C_6)$-alkoxy, fluorine, chlorine, nitro, —N$(R^{10})_2$, trifluoromethyl, hydroxyl, hydroxy-$(C_1-C_4)$-alkyl, $(C_1-C_4)$-alkoxycarbonyl, phenyl, phenoxy, benzyloxy and benzyl. Heteroaryl particularly preferably represents a monocyclic or bicyclic aromatic radical having 5 to 10 ring members, in particular a 5-membered or 6-membered monocyclic aromatic radical which contains 1, 2 or 3, in particular 1 or 2, identical or different heteroatoms from the group consisting of N, O and S and can be substituted by 1 or 2 identical or different substituents from the group consisting of $(C_1-C_4)$-alkyl, halogen, hydroxyl, —N$(R^{10})_2$, $(C_1-C_4)$-alkoxy, phenyl, phenoxy, benzyloxy and benzyl.

The expression "heterocycle having 5 to 12 ring members" represents a monocyclic or bicyclic 5-membered to 12-membered heterocyclic ring which is partly saturated or completely saturated. Examples of heteroatoms are N, O and S. The heterocycle is unsubstituted or substituted on one or more carbon atoms or on one or more heteroatoms by identical or different substituents. These substituents have been defined above for the radical heteroaryl. In particular, the heterocyclic ring is monosubstituted or polysubstituted, for example monosubstituted, disubstituted, trisubstituted or tetrasubstituted, on carbon atoms by identical or different radicals from the group consisting of ($C_1$-$C_8$)-alkyl, for example ($C_1$-$C_4$)-alkyl, ($C_1$-$C_8$)-alkoxy, for example ($C_1$-$C_4$)-alkoxy such as methoxy, phenyl-($C_1$-$C_4$)-alkoxy, for example benzyloxy, hydroxyl, oxo, halogen, nitro, amino or trifluoromethyl and/or it is substituted on the ring nitrogen atom(s) in the heterocyclic ring by ($C_1$-$C_8$)-alkyl, for example ($C_1$-$C_4$)-alkyl such as methyl or ethyl, by optionally substituted phenyl or phenyl-($C_1$-$C_4$)-alkyl, for example benzyl. Nitrogen heterocycles can also be present as N-oxides or as quaternary salts.

Examples of the expressions heteroaryl having 5 to 14 ring members or heterocycle having 5 to 12 ring members are radicals which are derived from pyrrole, furan, thiophene, imidazole, pyrazole, oxazole, isoxazole, thiazole, isothiazole, tetrazole, 1,2,3,5-oxathiadiazole 2-oxides, triazolones, oxadiazolones, isoxazolones, oxadiazolidinediones, triazoles, which are substituted by F, —CN, —$CF_3$ or —C(O)—O—($C_1$-$C_4$)-alkyl, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, carboline and benzo-fused, cyclopenta-, cyclohexa- or cyclohepta-fused derivatives of these heterocycles. Particularly preferred radicals are 2- or 3-pyrrolyl, phenylpyrrolyl such as 4- or 5-phenyl-2-pyrrolyl, 2-furyl, 2-thienyl, 4-imidazolyl, methylimidazolyl, for example 1-methyl-2-, -4- or -5-imidazolyl, 1,3-thiazol-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or dihydropyridinyl, pyrrolidinyl, for example 2- or 3-(N-methylpyrrolidinyl), piperazinyl, morpholinyl, thiomorpholinyl, tetrahydrothienyl or benzodioxolanyl.

The structural formula of α-amino acids is as follows:

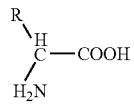

The α-amino acids differ from one another by the radical R, which in the context of the present application is described as a "characteristic radical" of an amino acid.

In the case where $R^8$ is the characteristic radical of an amino acid, the characteristic radicals employed are preferably those of the following naturally occurring α-amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid. Those particularly preferred are histidine, tryptophan, serine, threonine, cysteine, methionine, asparagine, glutamine, lysine, arginine, glutamic acid and aspartic acid. Preferred characteristic radicals of an amino acid which are furthermore employed as the radical $R^8$ are also non-naturally occurring amino acids such as 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, phenylglycine, 3-(2-thienyl)alanine, 3-(3-thienyl)alanine, 2-(2-thienyl)-glycine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl)alanine, 3-(1-naphthyl-alanine), homophenylalanine, homocysteine, homocysteic acid, homotryptophan, cysteic acid, 3-(2-pyridyl)alanine, 3-(3-pyridyl)alanine, 3-(4-pyridyl)alanine, 2-amino-3-phenylaminopropionic acid, 2-amino-3-phenylaminoethylpropionic acid, phosphinothricine, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide or —NH—$NR^{10}$—CON($R^{10}$)$_2$, which are optionally also substituted. In the case of natural but also of non-naturally occurring amino acids which have a functional group such as amino, hydroxyl, carboxyl, mercapto, guanidyl, imidazolyl or indolyl, this group can also be protected.

Suitable protective groups for this are preferably the N-protective groups customarily used in peptide chemistry, for example protective groups of the urethane type, benzyloxycarbonyl (Z), t-butoxycarbonyl (Boc), 9-fluorenyl-oxycarbonyl (Fmoc), allyloxycarbonyl (Aloc) or of the acid amide type, in particular formyl, acetyl or trifluoroacetyl, and of the alkyl type, for example benzyl. In the case of an imidazole radical in $R^8$, for example, the sulfonic acid derivative of the formula IV employed for the sulfonamide formation is used as a protective group of the imidazole nitrogen, which can be removed again, in particular in the presence of bases such as aqueous sodium hydroxide solution.

The starting substances for the chemical reactions are known or can be easily prepared by methods known from the literature.

The invention further relates to a process for preparing compounds of the formula I and/or a stereoisomeric form of the compound of the formula I and/or of a physiologically acceptable salt of the compound of the formula I, which comprises a) reacting a compound of the formula IV,

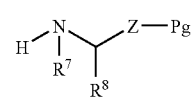

(IV)

in which Pg is a suitable protective group (for example methyl ester), an amide group or a hydroxyl group and Z, $R^7$ and $R^8$ are as defined in formula I with an acyl chloride or an activated ester of the compound of the formula III,

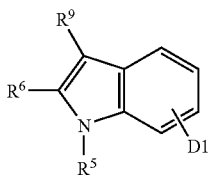

(III)

where D1 is —COOH or sulfonyl halogen and $R^5$, $R^6$ and $R^9$ are as defined in formula I in the presence of a base or, if appropriate, of a dehydrating agent in solution and, after removal of the protective group, converting into a compound of the formula I or b) reacting a compound of the formula IVa,

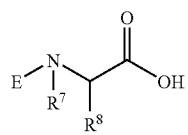

(IVa)

in which $R^7$ and $R^8$ are as defined in formula I and E is an N-amino protective group, with its carbonyl group coupled via an intermediate chain L to a polymeric resin of the formula PS, a compound of the formula V

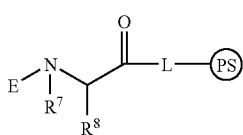

(V)

resulting, which, after selective removal of the protective group E, is reacted with a compound of the formula III, where $R^5$, $R^6$ and $R^9$ are as defined in formula I in the presence of a base or, if appropriate, of a dehydrating agent to give a compound of the formula VI

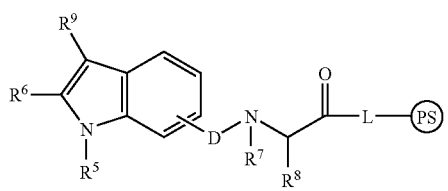

(VI)

and converting the compound of the formula VI, after cleavage from the support material, into a compound of the formula I or c) converting a compound of the formula I into a physiologically acceptable salt.

In process variant a), the acid functions of the compounds of the formula IVa are provided with a protective group Pg; this selective carboxylic acid derivatization is carried out according to methods such as are described in Houben-Weyl "Methoden der Org. Chemie" [Methods of Organic Chemistry], Volume 15/1. In process variant b), the amino functions of the starting compounds of the formula IVa are provided with a protective group E; this selective amino groups derivatization is carried out according to methods such as are described in Houben-Weyl "Methoden der Org. Chemie" [Methods of Organic Chemistry], Volume 15/1.

A suitable protective group Pg preferably used for this is the carboxyl protective groups customary in peptide chemistry, for example protective groups of the alkyl ester type, such as methyl, ethyl, tert-butyl, isopropyl, benzyl, fluorenylmethyl, allyl, aryl ester type, such as phenyl, amide type, such as amide or benzhydrylamine. Suitable protective groups E used for this are preferably the N-protective groups customary in peptide chemistry, for example protective groups of the urethane type, such as benzyloxycarbonyl (Z), t-butoxycarbonyl (Boc), 9-fluorenylmethoxycarbonyl (Fmoc) and allyloxycarbonyl (Aloc) or of the acid amide type, in particular formyl, acetyl or trifluoroacetyl of alkyl type such as benzyl.

The (trimethylsilyl)ethoxycarbonyl (Teoc) group has also proven particularly suitable for this (P. Kociénski, Protecting Groups, Thieme Verlag 1994).

The indolecarboxylic acid derivatives were prepared following a method described in Houben-Weyl "Methoden der Org. Chemie" [Methods of Organic Chemistry], Volume E6-2A and E6-2B. Thus, for preparing the indolecarboxylic acid derivatives of the formula III, preference is given to reacting hydrazinobenzoic acids and aryl ketones or heteroaryl ketones in the presence of polyphosphoric acid as solvent at 145° C. The hydrazinobenzoic acids required are prepared by methods known to the person skilled in the art, for example from the corresponding benzoic acid anilines. Aryl ketones or heteroaryl ketones are likewise prepared by methods familiar to the person skilled in the art, for example, from the corresponding acyl chlorides or nitriles by reaction with, for example, organometallic compounds.

For the condensation of the compounds of the formula IV with those of the formula III, the coupling methods which are well-known per se to the person skilled in the art are advantageously used (see, for example, Houben-Weyl, Methoden der Organischen Chemie [Methods of Organic Chemistry], Volume 15/1 and 15/2, Georg Thieme Verlag, Stuttgart, 1974). Suitable condensing agents or coupling reagents are compounds such as carbonyldiimidazole, carbodiimides such as dicyclohexylcarbodiimide or diisopropylcarbodiimide (DIC), O-((cyano(ethoxycarbonyl)methylene)-amino)-N,N,N',N'-tetramethyluronium tetrafluoroborate (TOTU) or propane-phosphonic anhydride (PPA).

The condensations can be carried out under standard conditions. During the condensation, as a rule it is necessary for the non-reacting amino groups present to be protected by reversible protective groups. The same applies to carboxyl groups not involved in the reaction, which during the condensation are preferably present as $(C_1-C_6)$-alkyl esters, benzyl esters or tert-butyl esters. Amino group protection is unnecessary if the amino groups are still present in the form of precursors such as nitro groups or cyano groups and are only formed by hydrogenation after the condensation. After the condensation, the protective groups present are removed in a suitable manner. For example, $NO_2$ groups (guanidino protection in amino acids), benzyloxycarbonyl groups and benzyl groups in benzyl esters can be removed by hydrogenation. The protective groups of the tert-butyl type are removed acidically, while the 9-fluorenylmethoxy-carbonyl radical is removed by secondary amines.

The polymeric support designated in the formulae V and VI by PS is a crosslinked polystyrene resin having a linker designated as the intermediate chain L. This linker carries a suitable functional group, for example amine, known, for example, as Rink amide resin, or an OH group, known, for example, as Wang resin or Kaiser's oxime resin. Alternatively, other polymeric supports such as glass, cotton or cellulose having various intermediate chains L can be employed.

The intermediate chain designated by L is covalently bonded to the polymeric support and allows a reversible, amide-like or ester-like bond with the compound of the formula IVa, which remains stable during the further reaction on the bonded compound of the formula IVa; but under strongly acidic reaction conditions, e.g. mixtures with trifluoroacetic acid, releases the group located on the linker again.

The release of the desired compound of the formula I from the linker can be carried out at various positions in the reaction sequence.

A. General Procedure for the Coupling of Protected Aminocarboxylic Acids of the Formula IVa to the Solid Support:

The synthesis was carried out in reactors each having a reaction volume of 15 ml. Each of the reactors was filled with 0.179 g of Rink amide AM resin (Fmoc-Rink amide AM/Nova-Biochem; loading 0.56 mmol/g; i.e. 0.1 mmol/reactor). For the removal of the Fmoc protective group from the resin, a 30% strength piperidine/DMF solution was metered into each reactor and the mixture was shaken for 45 minutes (min). It was then filtered and the resin was washed 3 times with dimethylformamide (DMF).

For the coupling of the protected amino acid, a 0.5 molar solution of the corresponding Fmoc-amino acid (0.3 mmol in DMF), a solution of HOBt (0.33 mmol in DMF) and a solution of DIC (0.33 mmol in DMF) were each added to the resin thus prepared and the mixture was shaken at 35° C. for 16 hours (h). The resin was then washed with DMF a number of times. To check the coupling, a few resin beads were removed and subjected to a KAISER test; in all cases the test was negative.

The removal of the Fmoc protective group was carried out, as mentioned above, using 30% strength piperidine/DMF solution.

For the coupling of the benzimidazolecarboxylic acids, a 0.1 molar solution of the corresponding 4- or 5-substituted acid (0.4 mmol in DMF); a 0.5 molar solution of the coupling reagent TOTU (0.44 mmol in DMF) and a 0.5 molar solution of DIPEA (0.6 mmol in DMF) were added and the mixture was shaken at 40° C. for 16 hours. It was then washed a number of times with DMF.

To check the reaction, a few beads of resin were again removed and subjected to a KAISER test.

For the removal of the desired substances from the solid support, the resin was washed a number of times with dichloromethane. The cleavage solution (50% dichloromethane and 50% of a mixture of 95% TFA, 2% $H_2O$, 3% triisopropylsilane) was then added and the mixture was shaken at room temperature for 1 h. The mixture was filtered and the filtrate was concentrated to dryness. The residue was precipitated with diethyl ether and filtered.

The solid residues usually contained the desired products in high purity or were fractionated, for example, on a reverse phase (eluent:A:$H_2O$/0.1% TFA, B:acetonitrile/0.1% TFA) using preparative high-pressure liquid chromatography. Lyophilization of the fractions obtained yielded the desired products.

The preparation of physiologically acceptable salts of compounds of the formula I capable of salt formation, including their stereoisomeric forms, is carried out in a manner known per se. With basic reagents such as hydroxides, carbonates, hydrogencarbonates, alkoxides and also ammonia or organic bases, for example trimethyl- or triethylamine, ethanolamine or triethanolamine or alternatively basic amino acids, for example lysine, ornithine or arginine, the carboxylic acids form stable alkali metal, alkaline earth metal or optionally substituted ammonium salts. If the compounds of the formula I contain basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, cyclohexyl-amidosulfonic, trifluoromethylsulfonic, acetic, oxalic, tartaric, succinic or trifluoroacetic acid are suitable.

The invention also relates to pharmaceuticals which comprise an efficacious amount of at least one compound of the formula I and/or of a physiologically tolerable salt of the compounds of the formula I and/or an optionally stereoisomeric form of the compounds of the formula I together with a pharmaceutically suitable and physiologically tolerable excipient, additive and/or other active compounds and auxiliaries.

On account of the pharmacological properties, the compounds according to the invention are suitable for the prophylaxis and therapy of all those disorders in whose course an increased activity of IkB kinase is involved. For example, compounds of the present invention are useful in the treatment of joint inflammation, Including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, chronic pulmonary inflammatory diseases including asthma and adult respiratory distress syndrome, silicosis, pulmonary sarcoidosis, bone resorption diseases, reperfusion injury, graft vs. host reaction, allograft rejection and leprosy. Furthermore, the compounds are useful in the treatment of infections such as viral infections, for example HIV, cytomegalovirus (CMV), influenza, adenovirus and the Herpes group of viruses, parasitic infections, for example malaria such as cerebral malaria, and yeast and fungal infections, for example fungal meningitis; fever and myalgias due to infection; AIDS; AIDS related complex (ARC); cachexia secondary to infection or malignancy; cachexia secondary to acquired immune deficiency syndrome (AIDS) or to cancer; keloid and scar tissue formation; pyresis; diabetes; and inflammatory bowel diseases such as Crohn's disease and ulcerative colitis. The compounds of the invention are also useful in the treatment of diseases of or injury to the brain in which over-expression of TNFα has been implicated such as multiple sclerosis, and head trauma. The compounds according to the invention are also useful in the treatment of psoriasis, Alzheimer's disease, carcinomatous disorders (potentiation of cytotoxic therapies), cardiac infarct, chronic obstructive pulmonary disease (COPD) and acute respiratory distress syndrome (ARDS).

The pharmaceuticals according to the invention are in general administered orally or parenterally. Rectal or transdermal administration is also possible.

The invention also relates to a process for the production of a pharmaceutical, which comprises bringing at least one compound of the formula I into a suitable administration form using a pharmaceutically suitable and physiologically tolerable excipient and, if appropriate, further suitable active compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions, and preparations having protracted release of active compound, in whose preparation customary auxiliaries, such as excipients, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower, groundnut or sesame oil, polyethylene glycol and solvents such as, for example, sterile water and mono- or polyhydric alcohols such as glycerol.

The pharmaceutical preparations are preferably produced and administered in dose units, each unit containing as active constituent a certain dose of the compound of the formula I according to the invention. In the case of solid dose units such as tablets, capsules, coated tablets or suppositories, this dose can be up to approximately 1000 mg, preferably from approximately 50 mg to 300 mg and in the case of injection solutions in ampoule form up to approximately 300 mg, preferably from approximately 10 mg to 100 mg.

For the treatment of an adult patient weighing approximately 70 kg, depending on the efficacy of the compound according to formula I, daily doses of approximately 20 mg to 1000 mg of active compound, preferably from approximately 100 mg to 500 mg, are indicated. Under certain circumstances, however, even higher or lower daily doses may be appropriate. The administration of the daily dose can be carried out both by single administration In the form of an individual dose unit or else of a number of smaller dose units and by multiple administration of subdivided doses at specific intervals.

As a rule, final products are determined by mass-spectroscopic methods (FAB-, ESI-MS). Temperatures are given in degrees Celsius, RT means room temperature (22-26° C.). Abbreviations used are either explained or correspond to the customary conventions.

EXAMPLES

Preparation of Substituted Indolecarboxylic Acids

Process Variant A)

2,3-Diphenyl-1H-indole-5-carboxylic acid 1.96 g (10 mmol) of deoxybenzoin and 1.52 g of 4-hydrazinobenzoic acid were ground in a mortar and then fused in an open flask at 160° C. for 15 minutes (min). The cooled melt was admixed with 100 ml of acetic acid and 30 ml of concentrated hydrochloric acid and heated under reflux for 3 hours (h). The cooled solution was admixed with water, resulting in the precipitation of the product 2,3-diphenyl-1H-indole-5-carboxylic acid. The product was filtered off with suction and the residue was washed with water and dried. For purification, the crude product was stirred with warm toluene, filtered off with suction and dried again. This gave 2,3-diphenyl-1H-indole-5-carboxylic acid.

Process Variant B)

2-Pyridin-4-yl-1H-indole-5-carboxylic acid 20 g of $P_2O_5$ were admixed with 12.5 ml of $H_3PO_4$ (85%), resulting in a strong increase of the temperature of the reaction mixture. The reaction mixture was then cooled to 60° C., and 8.90 g (65.84 mmol) of 4-propionylpyridine and 4.20 g (27.60 mmol) of 4-hydrazinobenzoic acid were added. The mixture was then stirred at 145° C. for 45 min. The reaction mixture was poured into water, resulting in the precipitation of the yellow product 2-pyridin-4-yl-1H-indole-5-carboxylic acid. This precipitate was filtered off with suction and washed with water until neutral. The 2-pyridin-4-yl-1H-indole-5-carboxylicacid, which was obtained by this method in quantitative yield, was used without further purification for coupling with amino acid derivatives.

Coupling of amino acid derivatives with substituted indolecarboxylic acid derivatives.

Process Variant C)

Example 1

N-(1-Carbamoyl-3-phenylpropyl)-2,3-diphenyl-1H-indole-5-carboxamide 0.16 g (0.5 mmol) of 2,3-diphenyl-1H-indole-5-carboxylic acid (see process variant A) was dissolved at RT in 10 ml of dry dimethylformamide (DMF) and admixed successively with 0.11 g (0.5 mmol) of L-homophenyl-alaninamide hydrochloride, 0.16 g of TOTU (O-[(cyano(ethoxycarbonyl)-methylidene)amino-1,1,3,3-tetramethyl]uronium tetrafluoroborate) and 0.14 ml (1 mmol) of diisopropylamine. The reaction mixture was stirred at RT for 6 h and then concentrated under reduced pressure, and the residue was dissolved in ethyl acetate. The organic phase was washed successively with water, saturated sodium carbonate solution, water and saturated sodium chloride solution, dried over magnesium sulfate, filtered and concentrated under reduced pressure. This gave N-(1-carbamoyl-3-phenylpropyl)-2,3-diphenyl-1H-indole-5-carboxamide of melting point 120° C. to 125° C.

Example 7

N-(1-Carbamoyl-3-pyrrol-1-ylpropyl)-3-methyl-2-pyridin-4-yl-1H-indole-5-carboxamide 0.13 g (0.5 mmol) of 3-methyl-2-pyridin-4-yl-1 H-indole-5-carboxylic acid (see process variant A) was dissolved at RT in 10 ml of dry dimethyl formamide (DMF) and mixed successively with 0.083 g (0.5 mmol) of 4-(1-pyrrolyl)-L-2-benzyloxycarbonylaminobutyramide, 0.16 g (0.5 mmol) of TOTU (O[(cyano(ethoxycarbonyl)methylidene)amino-1, 1,3,3,-tetramethyl] uronium tetrafluoroborate) and 0.14 ml (1 mmol) of ethyl diisopropylamine. The reaction mixture was stirred at RT for 6 h and then concentrated under reduced pressure, and the residue was dissolved in ethyl acetate. The organic phase was washed successively with water, saturated sodium carbonate solution, water and saturated sodium chloride solution, dried over magnesium sulfate, filtered and concentrated under reduced pressure. Purification was carried out by prep. HPLC.

a: 4-(1-Pyrrolyl)-L-2-benzyloxycarbonylaminobutyric acid

A solution, flushed with argon, of 1.25 g (5.0 mmol) of Nα-Z-L-2,4-diaminobutyric acid in 60 ml of water was admixed with 0.66 g (5.0 mmol) of 2,5-dimethoxytetrahydrofuran, followed by addition of 1.7 ml of glacial acetic acid, and the mixture was stirred at 20° C. for 12 h. The reaction mixture was extracted repeatedly with ethyl acetate, the organic phases were combined and dried with sodium sulfate and the filtrate was concentrated under reduced pressure. The crude product was purified by flash chromatography over silica gel ($CH_2Cl_2/CH_3OH/CH_3COOH$:100/5/1). Removal of the mobile phase gave 1.3 g (87%) of 4-(1-pyrrolyl)-L-2-benzyloxycarbonylaminobutyric acid.

b: 4-(1 Pyrrolyl)-L-2-benzyloxycarbonylaminobutyramide 1.2 g (4.0 mmol) of 4-(1-pyrrolyl)-L-2-benzyloxycarbonylaminobutyric acid and 0.61 g (4.0 mmol) of N-hydroxybenzotriazole ammonium salt, were dissolved together in 10 ml of DMF, admixed at 0° C. with 0.82 g (4.0 mmol) of N,N'-dicyclohexylcarbodiimide and 0.68 ml (4.0 mmol) of N-ethyldiisopropylamine, and the mixture was stirred at 0° C. for 30 min and at 20° C. for 3 h. The precipitated urea was filtered off with suction and the filtrate was concentrated to dryness under reduced pressure.

The crude product was purified by silica gel chromatography ($CH_2Cl_2/CH_3OH/CH_3COOH$:100/5/1). Yield: 0.89 g (74%).

c: 4-(1-Pyrrolyl)-L-2-aminobutyramide

Under inert gas, 0.80 g (2.65 mmol) of 4-(1-pyrrolyl)-L-2-benzyloxycarbonylaminobutyramide, dissolved in 20 ml of methanol, was admixed with 80 mg of catalyst (10% Pd—C), and hydrogen was then introduced until the Z protective group had been cleaved off completely.

The catalyst was filtered off and the filtrate was concentrated, giving 0.4 g (90.5%) of 4-(1-pyrrolyl)-L-2-aminobutyramide.

2. Process Variant D)

Example 3

N-(1-carbamoyl-2-phenylsulfanylethyl)-2-pyridin-4-yl-1H-indole-5-carboxamide 0.20 g (0.84 mmol) of 2-pyridin-4-yl-1H-indole-5-carboxylic acid was admixed with 0.21 g (1.07 mmol) of 2-amino-3-phenylsulfanylpropionic acid in 40 ml of DMF and, at 0° C., 0.66 g (1.27 mmol) of benzotriazol-1-yloxytripyrrolidinophosphonium hexafluorophosphate and 0.37 ml (2.12 mmol) of N-ethyl-N,N-diisopropylamine were added, and the solution was stirred at 20° C. for 2 h. The solution was concentrated under reduced pressure and purified by medium pressure column chromatography ($CH_2Cl_2/CH_3OH$:9:1). This gave 0.19 g (54%) of N-(1-carbamoyl-2-phenylsulfanylethyl)-2-pyridin-4yl-1H-indole-5-carboxamide.

Example 9

3-Phenylaminoethyl-2[(2-pyridin-4-yl-1H-indole-5-carbonyl)-amino]propionamide

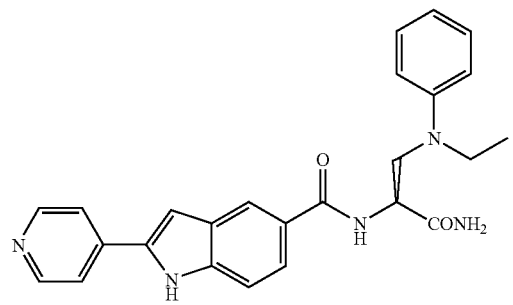

a) L-2-Amino-3-phenylaminoethylpropionic acid 54.8 g (0.209 mol) of triphenylphosphine were suspended in 600 ml of acetonitrile and, with exclusion of moisture, cooled to −35° C. to −45° C. At this temperature, 36.4 g (0.209 mol) of diethyl azodicarboxylate were then added dropwise over a period of 50 min. The mixture was stirred at −35° C. for another 15 min. A solution of 50 g (0.209 mol) of N-benzyloxycarbonyl-L-serine in 500 ml of acetonitrile was added dropwise to this mixture, the temperature being kept below −35° C. The mixture was then allowed to react at 5° C. for another 12 h and warmed to RT. The reaction solution was freed from solvent under reduced pressure and the crude product was purified by medium pressure chromatography over silica gel (DCM/AcCN:25/1). Removal of the solvent gave 20.8 g (yield 45%) of pure N-benzyloxycarbonyl-L-serine-β-lactone (see also Org. Synth. 1991 (70) 1ff.) in fine needles. Empirical formula $C_{11}H_{11}NO_4$; M.W.=221.2; MS (M+H) 222.1.

Under a protective atmosphere of argon, 15.5 ml (63.51 mmol) of N,O-bls(trimethylsilyl)acetamide were added to 7.3 ml (57.36 mmol) of N-ethylaniline in 250 ml of acetonitrile, and the mixture was stirred at 50° C. for 3 h. At 20° C., a solution of the above lactone (10.7 g, 48.37 mmol) dissolved in 250 ml of acetonitrile was then added, and the mixture was heated under reflux for 17 h. The solvent was removed and the residue was then admixed with saturated sodium carbonate solution, the pH of the solution being kept below 9. The aqueous suspension was washed with a little diethyl ether and then acidified to a pH of from 6 to 7 using conc. hydrochloric acid, and adjusted to a pH of 5 using $NaHPO_4$ buffer. The aqueous solution was then extracted repeatedly with ethyl acetate. Evaporation of the solvents gave the desired product in a yield of 45% (7.4 g). Empirical formula $C_{19}H_{22}N_2O_4$; M.W.=342.4; MS (M+H) 343.2.

At −10° C., 6.5 ml (89.1 mmol) of thionyl chloride were added dropwise to 75 ml of methanol, and the mixture was stirred for 30 min. 8.6 g (25.12 mmol) of L-2-aminoethyl-3-phenylaminopropionic acid, dissolved in 75 ml of methanol, were then added and the mixture was stirred at −10° C. for 30 minutes and at room temperature for a further 3 h. The solvents were evaporated and the residue was then taken up in ethyl acetate and washed with sodium carbonate solution. Evaporation of the solvent and purification by flash chromatography (n-heptan/ethyl acetate 7:3) gave 4.43 g (50% yield) of methyl L-2-aminoethyl-3-phenylaminopropionic acid. Empirical formula $C_{20}H_{24}N_2O_4$; M.W.=356.4; MS (M+H) 357.3.

To remove the protective group, 4.4 g (12.35 mmol) of the Z-protected derivative were dissolved in 500 ml of methanol, 100 mg of catalyst (10% Pd(OH)$_2$—C) were added under inert gas and hydrogen was introduced until the Z protective group had been cleaved off completely. The catalyst was filtered off and the filtrate was concentrated, giving 2.8 g of L-2-aminoethyl-3-phenylaminopropionic acid (quantitative).

Empirical formula $C_{12}H_{18}N_2O_2$; M.W.=223.3; MS (M+H) 223.1.

Process Step b)

0.63 g (2.64 mmol) of 2-pyridin-4-yl-1H-indole-5-carboxylic acid, prepared as in process variant B), was suspended in 150 ml of DMF and admixed successively with 1.01 g (3.08 mmol) of TOTU and 0.63 ml (3.71 mmol) of ethyidiisopropylamine. The mixture was stirred at RT for 20 min, and 0.73 g (3.28 mmol) of methyl (S)-2-amino-3-phenylaminoethylpropionate, prepared according to a), was added to the resulting clear solution. The mixture was stirred under reduced pressure for 15 h and the methyl ester of the title compound was then isolated by flash chromatography over silica gel (DCM:MeOH=19:1). Yield: 0.44 g, empirical formula $C_{26}H_{26}N_4O_3$; M.W.=442.2; MS (M+H) 443.3.

0.22 g (0.497 mmol) of the resulting methyl ester was dissolved in 100 ml of methanol and cooled to 0° C., and 1.5 h of ammonia were then introduced. The solution was allowed to stand at room temperature overnight and the methanol was then evaporated. The crude product was purified by flash chromatography over silica gel (DCM:MeOH=19:1). Yield: 0.096 g (45.2%), empirical formula $C_{25}H_{25}N_5O_2$; M.W.=427.2; MS (M+H) 428.3.

The compounds in Table 1 below were prepared analogously to Processes A) to D).

TABLE 1

| Example | Structure | Empirical formula | MS (M + H) | Notes |
|---|---|---|---|---|
| 1 | 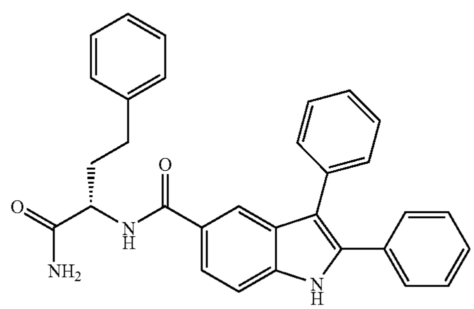 | M.W. = 473.58 $C_{31}H_{27}N_3O_2$ | 474.2 | pr.v.: A) pr.v.: C) |
| 2 | 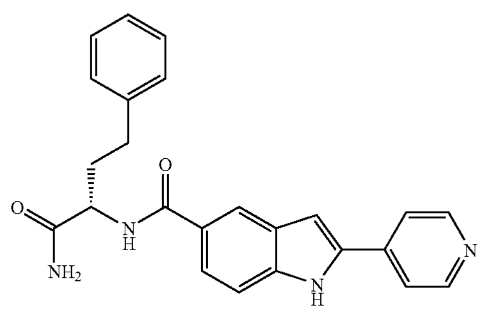 | M.W. = 398.46 $C_{24}H_{22}N_4O_2$ | 399.3 | pr.v.: B) pr.v.: C) |
| 3 | 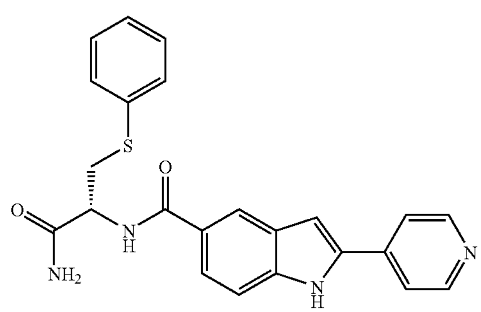 | M.W. = 416.50 $C_{23}H_{20}N_4O_2S$ | 417.1 | pr.v.: A) pr.v.: D) |

TABLE 1-continued

| Example | Structure | Empirical formula | MS (M + H) | Notes |
|---------|-----------|-------------------|------------|-------|
| 4 | 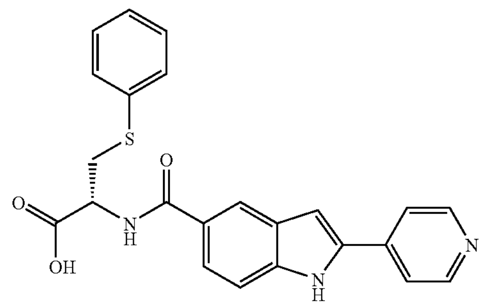 | M.W. = 417.9<br>$C_{23}H_{19}N_3O_3S$ | 418.1 | pr.v.: B)<br>pr.v.: C) |
| 5 | 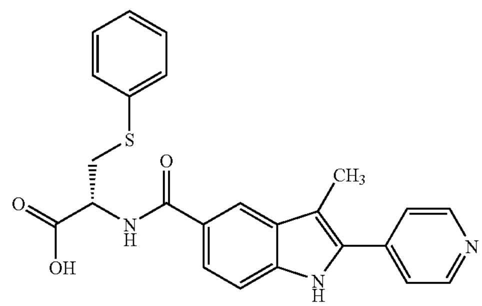 | M.W. = 431.51<br>$C_{24}H_{21}N_3O_3S$ | 432.1 | pr.v.: B)<br>pr.v.: C) |
| 6 | 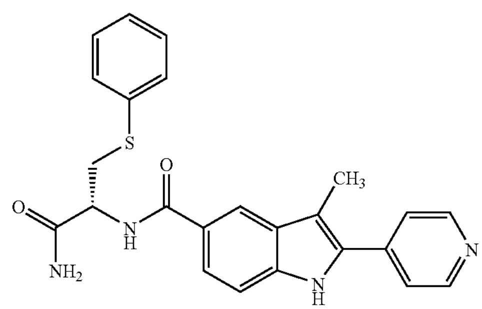 | M.W. = 430.53<br>$C_{24}H_{22}N_4O_2S$ | 431.2 | pr.v.: B)<br>pr.v.: C) |
| 7 | 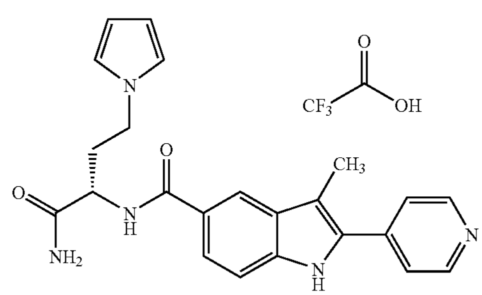 | M.W. = 518.47<br>$C_{23}H_{22}N_4O_3 \cdot$<br>$C_2HF_3O_2$ | 403.2 | pr.v.: B)<br>pr.v.: C) |
| 8 | 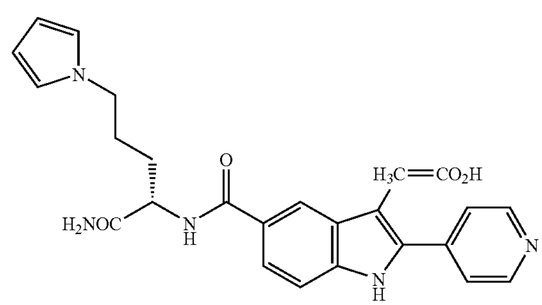 | M.W. = 475.50<br>$C_{24}H_{25}N_5O_2 \cdot$<br>$C_2H_4O_2$ | 416.5 | pr.v.: B)<br>pr.v.: C) |

TABLE 1-continued

| Example | Structure | Empirical formula | MS (M + H) | Notes |
|---|---|---|---|---|
| 9 | | M.W. = 427.2; $C_{25}H_{25}N_5O_2$ | 428.3 | | pr.v. = process variant

Pharmacological Examples IκB Kinase ELISA

The activity of the IκB kinase was determined using an ELISA comprising a biotinilated substrate peptide containing the amino acid sequence in the protein IκB of serines 32 to 36 and a specific poly- or monoclonal antibody (for example from New England Biolabs, Beverly, Mass., USA, cat.: 9240), which binds only to the phosphorylated form of the peptide IκB. This complex was immobilized on an antibody-binding plate (coated with protein A) and detected using a conjugate of a biotin-binding protein and HRP (for example streptavidine HRP). The activity could be quantified using a standard curve with substrate phosphopeptide.

Procedure

To obtain the kinase complex, 10 ml of HeLa S3 cell extract S100 were diluted with 40 ml 50 mM HEPES, pH 7.5, adjusted to 40% ammonium sulfate and incubated on ice for 30 minutes. The precipitated pellet was dissolved in 5 ml SEC buffer (50 mM HEPES, pH 7.5, 1 mM DTT, 0.5 mM EDTA, 10 mM 2-glycerophosphate), centrifuged at 20,000×g for 15 minutes and filtered through a 0.22 μm filter. The sample was applied to a 320 ml Superose-6 FPLC column (Amersham Pharmacia Biotech AB, Uppsala, Sweden) which had been equilibrated with SEC buffer and was operated at a flow rate of 2 ml/min at 4° C. The fractions which corresponded to the elution time of the 670 kDa molecular weight standard were combined for activation. Activation was achieved by a 45-minute-incubation with 100 nM MEKK1Δ, 250 μM MgATP, 10 mM $MgCl_2$, 5 mM dithiothreitol (DTT), 10 mM 2-glycerophosphate, 2.5 μM microcystin LR at 37° C. The activated enzyme was stored at −80° C.

The test substances, dissolved in DMSO (2 μl), were preincubated at 25° C. with 43 μl of activated enzyme (diluted 1:25 in reaction buffer 50 mM HEPES, pH 7.5, 10 mM $MgCl_2$, 5 mM DTT, 10 mM β-glycerophosphate, 2.5 μM microcystin LR) for 30 minutes. 5 μl of substrate peptide (biotin-$(CH_2)_6$-DRHDSGLDSMKD-$CONH_2$) (200 μM) were added, the mixture was incubated for one hour and the reaction was quenched using 150 μl of 50 mM HEPES, pH 7.5, 0.1% BSA, 50 mM EDTA, antibody [1:200]. 100 μl of the quenched reaction mixture or a standard phosphopeptide dilution series (biotin-$(CH_2)_6$-DRHDS[$PO_3$]GLDSMKD-$CONH_2$) were then transferred to a protein A plate (Pierce Chemical Co., Rockford, Ill., USA) and incubated with shaking for 2 hours.

After 3 washing steps with PBS, 100 μl of 0.5 μg/ml of streptavidin HRP (horseradish peroxidase) (diluted in 50mM HEPES/0.1% BSA) were added for 30 minutes. After 5 washing steps with PBS, 100 μl of TMB substrate (Kirkegaard & Perry Laboratories, Gaithersburg, Md., USA) were added and the development of color was stopped by addition of 100 μl of 0.18 M sulfuric acid. Absorption was measured at 450 nm. The standard curve was generated by linear regression according to a 4-parameter dose-activity relation. Using this standard curve, the enzyme activity or their inhibition by test substances was quantified.

Method PKA, PKC, CK II cAMP-dependent protein kinase (PKA), protein kinase C (PKC) and casein kinase II (CK II) were determined using the corresponding test kits of Upstate Biotechnologie according to the instructions of the manufacturer at an ATP concentration of 50 μM. However, instead of phosphocellulose filters, multi-screen plates (Millipore; Phosphocellulose MS-PH, cat. MAPHNOB10) with the corresponding aspiration system were used. The plates were then measured in a Wallac MicroBeta scintillation counter. In each case, 100 μM of test substance were used.

Each substance was tested in duplicate. The mean of the blank (without enzyme) was subtracted from the means (enzyme with and without substances), and the inhibition in % was calculated. $IC_{50}$ calculations were carried out using the software package GraFit 3.0. The results are shown in Table 2 below.

TABLE 2

| | Kinase inhibition at a substance concentration of 100 μM or $IC_{50}$ in μM | | | |
|---|---|---|---|---|
| Example number | IκB kinase $IC_{50}$ | PKA % inhibition | PKC % inhibition | CK II % inhibition |
| 1 | 32 | n.d. | n.d. | n.d. |
| 2 | 0.61 | 24 | 15 | 35 |
| 3 | 0.55 | 35 | 39 | 37 |
| 4 | 0.50 | 42 | 33 | 47 |
| 5 | 1.8 | 55 | 8 | 27 |
| 6 | 4.9 | 60 | 58 | 39 |
| 7 | 3.0 | n.d. | n.d. | 18 |
| 9 | 1.0 | 0 | 23 | 0 | n.d. means not determined.

We claim:

1. A compound of the formula I

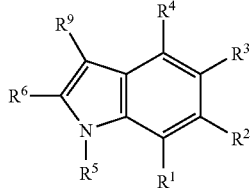

in any stereoisomeric form, or a physiologically acceptable salt thereof, wherein $R^1$, $R^2$ and $R^4$ are, independently, hydrogen, halogen, or aryl;

$R^5$ is hydrogen;

$R^3$ is a radical of formula II

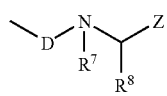

wherein,

D is —C(O)—;

$R^7$ is hydrogen;

$R^8$ is —$(C_1$-$C_6)$-alkyl, wherein alkyl is straight-chain or branched and is unsubstituted or mono-, di- or trisubstituted, independently of one another, by —$N(R^{10})_2$, wherein each $R^{10}$ is, independently, hydrogen, —$(C_1$-$C_4)$-alkyl, aryl, or a heterocycle having 5 to 12 ring members; and Z is —$CONH_2$ or —COO—$R^{10}$ or a monocyclic or bicyclic 5-membered to 12-membered heterocyclic ring which is partly saturated or completely saturated, wherein said heterocycle is unsubstituted or monosubstituted, disubstituted, trisubstituted or tetrasubstituted on carbon atoms by identical or different radicals from the group consisting of $(C_1$-$C_8)$-alkyl, phenyl-$(C_1$-$C_4)$-alkoxy, hydroxyl, oxo, halogen, nitro, amino or trifluoromethyl;

$R^9$ is, independently, any substituent identified above for $R^8$; and $R^6$ is a heterocycle having 5 to 12 ring members, which is unsubstituted or substituted by —CN, —$CF_3$, halogen, —O—$R^{10}$, —$N(R^{10})_2$, —NH—C(O)—$R^{11}$, —$S(O)_x$—$R^{10}$, wherein x is the integer zero, 1 or 2, —C(O)—$R^{11}$ or —$(C_1$-$C_4)$-alkyl-$NH_2$, and wherein $R^{10}$ is as defined above and $R^{11}$ is —O—$R^{10}$ or —$N(R^{10})_2$.

2. The compound according to claim 1, wherein Z is pyrrole, furan, thiophene, imidazole, pyrazole, oxazole, isoxazole, thiazole, isothiazole, tetrazole, 1,2,3,5-oxathiadiazole 2-oxide, triazolone, oxadiazolone, isoxazolone, oxadiazolidinedione, triazole, 3-hydroxypyrrole-2,4-dione, 5-oxo- 1,2,4-thiadiazole, pyridine, pyrazine, pyrimidine, indole, isoindole, indazole, phthalazine, quinoline, isoquinoline, quinoxaline, quinazoline, cinnoline, carboline or a benzo-fused or cyclopenta-, cyclohexa- or cyclohepta-fused derivative of any of the above heterocycles, which is unsubstituted or substituted by $(C_1$-$C_4)$-alkyl, methoxy, benzyloxy, hydroxyl, oxo, halogen, nitro, amino or trifluoromethyl.

3. The compound according to claim 1, wherein Z is oxazole, isoxazole, 1,2,3,5-oxathiadiazole 2-oxide, oxadiazolone, isoxazolone, oxadiazolidinedione, 3-hydroxypyrrole-2,4-dione, 5-oxo-1,2,4-thiadiazole or 1,3,4-oxadiazole, which is unsubstituted or substituted by $(C_1$-$C_4)$-alkyl, methoxy, benzyloxy, hydroxyl, oxo, halogen, nitro, amino or trifluoromethyl.

4. The compound according to claim 1, wherein $R^8$ is —$CH_2$—N(phenyl)$_2$.

5. The compound according to claim 1, wherein $R^6$ is pyrrole, furan, thiophene, imidazole, pyrazole, oxazole, isoxazole, thiazole, isothiazole, tetrazole, 1,2,3,5-oxathiadiazole 2-oxide, triazolone, oxadiazolone, isoxazolone, oxadiazolidinedione, triazole, 3-hydroxypyrrole-2,4-dione, 5-oxo-1,2,4-thiadiazole, pyridine, pyrazine, pyrimidine, indole, isoindole, indazole, phthalazine, quinoline, isoquinoline, quinoxaline, quinazoline, cinnoline, carboline or a benzo-fused or cyclopenta-, cyclohexa- or cyclohepta-fused derivative of any of the above heterocycles, which is unsubstituted or substituted by —$N(R^{10})_2$, wherein $R^{10}$ is —$(C_1$-$C_4)$-alkyl.

6. The compound according to claim 1, wherein $R^6$ is unsubstituted or substituted pyrrole, pyrazole, pyridine, pyrazine or pyrimidine.

7. The compound according to claim 1, wherein $R^1$, $R^2$ and $R^4$ are hydrogen.

8. A compound of formula I

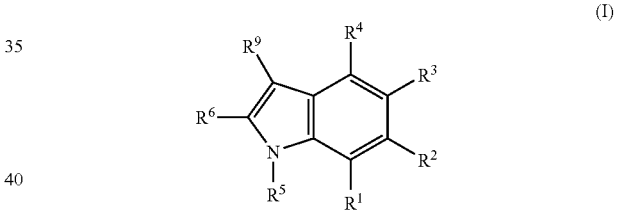

in any stereoisomeric form, or a physiologically acceptable salt thereof, wherein, one of $R^1$, $R^2$, $R^3$ and $R^4$ is a radical of the formula II,

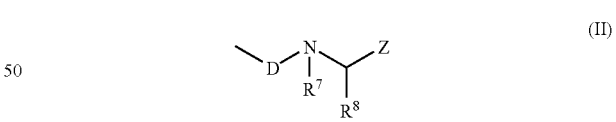

wherein,

D is —C(O)—;

$R^7$ is hydrogen or —$(C_1$-$C_4)$-alkyl;

$R^8$ is the characteristic radical of an amino acid, or —$(C_1$-$C_4)$-alkyl, wherein alkyl is straight-chain or branched and is mono- or disubstituted, independently of one another, by heteroaryl having 5 to 14 ring members, wherein heteroaryl is unsubstituted or substituted, heterocycle having 5 to 12 ring members, wherein heterocycle is unsubstituted or substituted,

—O—$R^{10}$,

—$S(O)_x$—$R^{10}$, wherein x is the integer zero, 1 or 2,

—$N(R^{10})_2$, radical of the formula

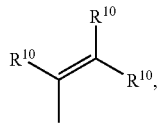

or
radical of the formula

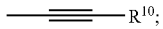

$R^9$ is $R^8$, aryl, wherein the aryl is unsubstituted or substituted, or —($C_1$-$C_4$)-alkyl, wherein the alkyl is straight-chain or branched and is, independently of one another, mono-, di- or trisubstituted by
aryl, wherein the aryl is unsubstituted or substituted,
halogen,
—CN or
—$CF_3$;
$R^{10}$ is hydrogen, aryl, heteroaryl having 5 to 14 ring members, heterocycle having 5 to 12 ring members, or —($C_1$-$C_6$)-alkyl, wherein the alkyl is unsubstituted or mono- to trisubstituted, independently of one another, by
aryl,
heteroaryl having 5 to 14 ring members,
heterocycle having 5 to 12 ring members,
halogen,
—N—($C_1$-$C_6$)$_n$-alkyl, where n is the integer zero, 1 or 2 and alkyl is unsubstituted or mono-, di- or trisubstituted, independently of one another, by halogen or by —C(O)—OH, or —C(O)—OH;
and in the case of $(R^{10})_2$, $R^{10}$, independently of one another, has the meaning of hydrogen, aryl, heteroaryl having 5 to 14 ring members, heterocycle having 5 to 12 ring members, or —($C_1$-$C_6$)-alkyl, wherein the alkyl is unsubstituted or mono- to trisubstituted, independently of one another, by
aryl,
heteroaryl having 5 to 14 ring members,
heterocycle having 5 to 12 ring members,
halogen,
—N—($C_1$-$C_6$)$_n$-alkyl, where n is the integer zero, 1 or 2 and alkyl is unsubstituted or mono-, di- or trisubstituted, independently of one another, by halogen or by —C(O)—OH, or
—C(O)—OH;
Z is —C(O)—$R^{11}$ wherein the $R^{11}$ is —O—$R^{10}$ or —N($R^{10}$)$_2$, or
1,3,4-oxadiazole, where 1,3,4-oxadiazole is unsubstituted or mono- to trisubstituted by —$NH_2$, OH or —($C_1$-$C_4$)-alkyl;
$R^7$ and $R^8$ form, together with the nitrogen atom and carbon atom to which they are each bonded, a ring of the formula IIa selected from the group consisting of pyrrole, pyrroline, pyrrolidine, pyridine, piperidine, piperylene, pyridazine, pyrimidine, pyrazine, piperazine, pyrazole, imidazole, pyrazoline, imidazoline,
pyrazolidine, imidazolidine, oxazole, tetrazole, 1,2,3,5-oxathiadiazole 2-oxides, triazolones, oxadiazolones, isoxazolones, oxadiazolidinediones, triazoles, which are unsubstituted or substituted by F,
—CN, —$CF_3$ or C(O)—O—($C_1$-$C_4$)-alkyl, 3-hydroxypyrrole-2,4-diones, 5-oxo-1,2,4-thiadiazoles, isoxazoles, 2-isoxazolidine, isoxazolidine, morpholine, isothiazole, thiazole, isothiazolidine, thiomorpholine, indazole, thiadiazole, benzimidazole, quinoline, triazole, phthalazine, quinazoline, quinoxaline, purine, pteridine, indole, isoquinoline, tetrahydroquinoline and tetrahydroisoquinoline;
$R^8$ and Z form, together with the carbon atoms to which they are each bonded, a ring of the formula Iic
selected from the group consisting of pyrrole, pyrroline, pyrrolidine, pyridine, piperidine, pyrazoline, phthalazine, piperylene, pyridazine, pyrimidine, pyrazine, piperazine, pyrazole, imidazole, 1,3,4-oxadiazole, imidazoline, pyrazolidine, imidazolidine, oxazole, isoxazole, 2-isoxazolidine, isoxazolidine, morpholine, isothiazole, thiazole, isothiazolidine, thiomorpholine, indazole, thiadiazole, benzimidazole, quinoline, triazole, tetrazole, 1,2,3,5-oxathiadiazole 2-oxides, oxadiazolones, isoxazolones, triazolones, oxadiazolidindiones, triazoles, which are unsubstituted or substituted by F, —CN, —$CF_3$ or
—C(O)—O—($C_1$-$C_4$)-alkyl, 3-hydroxypyrrole-2,4-diones, 5-oxo-1,2,4-thiadiazoles, quinazoline, quinoxaline, purine, indole, pteridine, tetrahydroquinoline, tetrahydroisoquinoline and isoquinoline;
the other $R^1$, $R^2$, $R^3$ and $R^4$ in each case independently of one another, are hydrogen, halogen, aryl, wherein the aryl is unsubstituted or substituted, heteroaryl having 5 to 14 ring members, wherein the heteroaryl is unsubstituted or substituted, heterocycle having 5 to 12 ring members, wherein the heterocycle is unsubstituted or substituted, —($C_1$-$C_6$)-alkyl, —CN, —$CF_3$, —O—$R^{10}$, —N($R^{10}$)$_2$, or —S(O)$_x$—$R^{10}$, wherein the x is the integer zero, 1 or 2;
$R^5$ is hydrogen; and
$R^6$ is phenyl, mono- or disubstituted, independently of one another, by —CN, —$CF_3$, halogen, —O—$R^{10}$, —N($R^{10}$)$_2$, —NH—C(O)—$R^{11}$, —S(O)$_x$—$R^{10}$, wherein x is the integer zero, 1 or 2, —C(O)—$R^{11}$ or —($C_1$-$C_4$)-alkyl-$NH_2$, heteroaryl having 5 to 14 ring members, wherein the heteroaryl is unsubstituted or mono-, di-or trisubstituted, independently of one another, by —CN, —$CF_3$, halogen, —O—$R^{10}$, —N($R^{10}$)$_2$, —NH—C(O)—$R^{11}$, —S(O)$_x$—$R^{10}$, wherein x is the integer zero, 1 or 2, —C(O)—$R^{11}$ or —($C_1$-$C_4$)-alkyl-$NH_2$, or
heterocycle having 5 to 12 ring members, wherein the heterocycle is unsubstituted or mono-, di- or trisubstituted, independently of one another, by —CN, —$CF_3$, halogen, —O—$R^{10}$, —N($R^{10}$)$_2$, —NH—C(O)—$R^{11}$, —S(O)$_x$—$R^{10}$, wherein x is the integer zero, 1 or 2, —C(O)—$R^{11}$ or —($C_1$-$C_4$)-alkyl-$NH_2$.

* * * * *